(12) United States Patent
Yao et al.

(10) Patent No.: US 11,883,570 B2
(45) Date of Patent: Jan. 30, 2024

(54) BLOOD TRANSFUSION KIT AND SYSTEM AND METHOD

(71) Applicant: TERUMO KABUSHIKI KAISHA, Tokyo (JP)

(72) Inventors: Takayoshi Yao, Shizuoka (JP); Kaoru Hosoe, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 468 days.

(21) Appl. No.: 16/648,000

(22) PCT Filed: Sep. 27, 2018

(86) PCT No.: PCT/JP2018/035892
§ 371 (c)(1),
(2) Date: Mar. 17, 2020

(87) PCT Pub. No.: WO2019/065823
PCT Pub. Date: Apr. 4, 2019

(65) Prior Publication Data
US 2020/0261631 A1 Aug. 20, 2020

(30) Foreign Application Priority Data
Sep. 28, 2017 (JP) .................. 2017-187420

(51) Int. Cl.
*A61M 1/02* (2006.01)
*A61M 39/28* (2006.01)
*A61M 39/22* (2006.01)

(52) U.S. Cl.
CPC ........ *A61M 1/0222* (2014.02); *A61M 39/223* (2013.01); *A61M 39/28* (2013.01); *A61M 2202/0439* (2013.01)

(58) Field of Classification Search
CPC .. A61M 1/0222; A61M 39/223; A61M 39/28; A61M 2202/0439; A61M 1/0218; A61M 1/02
See application file for complete search history.

(56) References Cited

U.S. PATENT DOCUMENTS 4,997,577 A * 3/1991 Stewart ............... A61M 1/0222
604/406
5,128,048 A * 7/1992 Stewart ............... A61M 1/0222
210/806

(Continued)

FOREIGN PATENT DOCUMENTS

CN 201036634 3/2008
CN 202554573 11/2012

(Continued)

OTHER PUBLICATIONS

Translation of JP 2007029272, retrieved from Espacenet on Jul. 16, 2022. <https://worldwide.espacenet.com/patent/search/family/037789238/publication/JP2007029272A?q=pn%3DJP2007029272A>. (Year: 2022).*

(Continued)

*Primary Examiner* — Tasnim Mehjabin Ahmed
(74) *Attorney, Agent, or Firm* — Sheridan Ross P.C.

(57) ABSTRACT

In a blood transfusion system (a blood transfusion kit, a blood transfusion kit for emergency blood transfusion, or a method of using a blood transfusion kit), a flow path through which blood flows is formed using a tube having a channel therein. The flow path includes: a first path that connects an upstream path and a downstream path and has a leukocyte removal filter removing leukocytes at an intermediate position of the channel; and a second path that connects the upstream path and the downstream path and bypasses the leukocyte removal filter.

20 Claims, 5 Drawing Sheets

(56) References Cited

U.S. PATENT DOCUMENTS

| | | | | |
|---|---|---|---|---|
| 5,527,472 A | * | 6/1996 | Bellotti | A61M 1/0222 210/194 |
| 2004/0147865 A1 | * | 7/2004 | Cianci | B04B 5/0442 494/37 |
| 2004/0200775 A1 | * | 10/2004 | Fukuda | A61M 1/0218 210/85 |
| 2007/0043317 A1 | * | 2/2007 | Sugawara | A61M 1/0231 604/406 |
| 2014/0228709 A1 | | 8/2014 | Hayakawa et al. | |

FOREIGN PATENT DOCUMENTS

| | | | |
|---|---|---|---|
| CN | 202554599 | | 11/2012 |
| CN | 203355011 | | 12/2013 |
| CN | 103861161 | | 6/2014 |
| CN | 203828945 | | 9/2014 |
| CN | 203828946 | | 9/2014 |
| CN | 104582669 | | 4/2015 |
| CN | 106964021 | | 7/2017 |
| JP | 11-164884 A | | 6/1999 |
| JP | 11-319084 A | | 11/1999 |
| JP | 11319084 A | * | 11/1999 |
| JP | 2001070443 A | | 3/2001 |
| JP | 200729272 A | | 2/2007 |
| WO | WO 2011/093260 | | 8/2011 |

OTHER PUBLICATIONS

Translation of JPH 11319084, retrieved from Espacenet on Jul. 16, 2022. <https://worldwide.espacenet.com/patent/search/family/015312827/publication/JPH11319084A?q=jph11319084>. (Year: 2022).*

Official Action (with English translation) for China Patent Application No. 201880052438.0, dated Apr. 19, 2022, 27 pages.

Official Action (with English translation) for China Patent Application No. 2018800524380, dated Oct. 9, 2021, 22 pages.

Official Action (with English translation) for China Patent Application No. 201880052438.0, dated Sep. 8, 2022, 25 pages.

Official Action with English Translation for Japan Patent Application No. 2019-545603, dated May 9, 2023, 12 pages.

* cited by examiner

BLOOD TRANSFUSION KIT AND SYSTEM AND METHOD

TECHNICAL FIELD

The present invention relates to a blood transfusion kit, a blood transfusion system, a blood transfusion kit for emergency blood transfusion, and a method of using a blood transfusion kit which are used for blood transfusion to a blood transfusion target.

Background Art

In blood transfusion, blood components (erythrocytes, plasma, platelets, or the like) from which leukocytes have been removed are usually administered to a patient (blood transfusion target). This is because transfusion side effects are suppressed by removing the leukocytes. However, there is a case where whole blood provided by a donor is transfused regardless of blood components when the blood transfusion is performed urgently due to massive bleeding or the like.

In addition, for example, a rapid infusion kit as disclosed in Japanese Utility Model Registration No. 3005461 is cited as a blood transfusion system used for emergency blood transfusion. This rapid infusion kit is provided with a pump section driven by applying an external pressure or releasing the external pressure in the middle of an infusion path, and performs a required amount of infusion at a required speed by the pump section.

SUMMARY OF INVENTION

Meanwhile, the rapid infusion kit disclosed in Japanese Utility Model Registration No. 3005461 is neither a configuration provided with a leukocyte removal filter nor a configuration capable of switching between normal use and emergency use in one system. Thus, for example, when a large amount of blood transfusion is urgently required during normal blood transfusion that removes leukocytes, it is necessary to remove a blood transfusion system for the normal time and newly connect a rapid blood transfusion kit again. In particular, when an emergency system is constructed in a situation where prompt treatment is required, the burden also increases by making a medical staff impatient.

The present invention has been made in view of the above circumstances, and an object thereof is to provide a blood transfusion kit, a blood transfusion system, a blood transfusion kit for emergency blood transfusion, and a method of using a blood transfusion kit which are convenient to use by enabling transfusion of whole blood easily during an emergency or the like while performing safe blood transfusion during the normal time.

In order to achieve the above object, the present invention provides a blood transfusion kit, which forms a channel through which blood flows using a tube structure and administers the blood to a blood transfusion target through the channel, including: a blood bag containing blood collected from a donor; a filter that removes leukocytes in the blood; a blood transfusion unit configured to transfuse blood from which the leukocytes have been removed by the filter to the blood transfusion target; a first channel connecting the blood bag and the filter; a second channel connecting the filter and the blood transfusion unit; and a bypass channel connecting the first channel and the second channel and bypassing the filter.

According to the above configuration, the blood transfusion kit can perform blood transfusion from which the leukocytes have been removed by the filter by causing the blood to flow through the first channel and the second channel during the normal time. As a result, it is possible to implement safe blood transfusion that suppresses transfusion side effects of the blood transfusion target. In addition, the blood transfusion kit can rapidly administer a large amount of blood without passing through the leukocyte removal filter by causing the blood to flow through the bypass channel during the emergency. That is, the blood transfusion kit can easily switch between a route passing through the filter and a route that does not pass through the filter, and thus, becomes more convenient to use, so that it is possible to reduce the work burden on the medical staff and to speed up medical treatment.

Further, it is preferable that a clamp capable of opening and closing each channel be provided on each of a downstream side of the first channel from a branch point of the bypass channel and the bypass channel.

The blood transfusion kit can easily switch between closing and opening of the channel as the medical staff operates the clamps provided respectively on the downstream side of the first channel from the branch point of the bypass channel and the bypass channel.

Here, it is preferable that the blood transfusion unit include an end connector that is provided at an end of the second channel and attachable to an introduction unit constructed for the blood transfusion target.

Since the end connector of the blood transfusion kit is easily connected to the introduction unit constructed for the blood transfusion target, the blood transfusion can be started for a shorter period of time.

Alternatively, the blood transfusion unit may be an administration needle that is provided at an end of the second channel, is directly inserted into the blood transfusion target, and is capable of administering blood to the blood transfusion target in the inserted state.

As a result, the blood transfusion kit can easily start blood transfusion by inserting the administration needle into the blood transfusion target.

In addition, it is preferable that the second channel be provided with an air vent unit that discharges air inside the channel and regulates outflow of blood inside the channel.

Since the blood transfusion kit has the air vent unit, it is possible to automatically and easily implement priming before the start of blood transfusion.

Furthermore, it is preferable that the first channel, the second channel, and the bypass channel allow blood to flow without stagnation.

The blood transfusion kit can rapidly perform a large amount of blood transfusion to the blood transfusion target since the first channel, the second channel, and the bypass channel are configured to have no blood stagnation (for example, there is no configuration such as storing blood components in a bag).

Further, it is preferable to provide a blood collection needle to be inserted into the donor and a blood collection channel connecting the blood collection needle and the blood bag.

Since the blood collection channel is connected to the blood bag, the blood transfusion kit can immediately perform blood transfusion from the blood bag after storing the blood of the donor.

In addition, in order to achieve the above object, the present invention provides a blood transfusion system, which forms a channel through which blood flows using a tube structure and is configured to transfuse blood collected from a donor through the channel, including: a blood collection unit that collects the blood from the donor; a blood bag containing blood collected from the donor; a blood collection channel connecting the blood collection unit and the blood bag; a filter that removes leukocytes in the blood; a blood transfusion unit configured to transfuse blood from which the leukocytes have been removed by the filter to a blood transfusion target; a first channel connecting the blood bag and the filter; a second channel connecting the filter and the blood transfusion unit; and a bypass channel connecting the first channel and the second channel and bypassing the filter. The second channel is provided with a connecting portion configured for connection with the blood transfusion unit at one end, and the blood transfusion unit is provided with a connected portion which is connected to the connecting portion.

In this case, it is preferable that the first channel have a clamp capable of opening and closing the channel between a branch point of the bypass channel and the filter.

It is preferable that the bypass channel have a clamp capable of opening and closing the channel, and that the bypass channel be set to a state where the channel is closed in an initial state.

Further, in order to achieve the above object, the present invention provides a blood transfusion kit for emergency blood transfusion including a main body that collects blood from a donor, and an administration kit that administers the collected blood to a blood transfusion target in order to transfuse the blood collected from the donor. The main body and the administration kit form a channel through which the blood flows using a tube structure. The main body includes: a blood collection unit that collects blood from the donor; a blood bag containing the blood collected from the donor; a blood collection channel connecting the blood collection unit and the blood bag; a filter that removes leukocytes in the blood; a first channel connecting the blood bag and the filter; a second channel that extends on a downstream side of the filter and is provided with a connecting portion, connected to the administration kit, at an end; and a bypass channel connecting the first channel and the second channel and bypassing the filter. The administration kit includes: an administration portion configured to transfuse the blood into the blood transfusion target; and a connected portion connected to the connecting portion. The main body and the administration kit are integrally packaged.

Furthermore, in order to achieve the above-described object, the present invention provides a method of using a blood transfusion kit, which forms a channel through which blood flows using a tube structure and administers the blood to a blood transfusion target through the channel. The blood transfusion kit includes: a blood bag containing blood collected from a donor; a filter that removes leukocytes in the blood; a blood transfusion unit configured to transfuse blood from which the leukocytes have been removed by the filter to the blood transfusion target; a first channel connecting the blood bag and the filter; a second channel connecting the filter and the blood transfusion unit; and a bypass channel connecting the first channel and the second channel and bypassing the filter. When using the blood transfusion kit, a first state in which the blood is administered through the filter by opening the first channel and closing the bypass channel, and a second state in which the blood is administered without passing through the filter by opening the bypass channel and closing a downstream side of the first channel from a branch point of the bypass channel are selectively switched.

According to the present invention, the blood transfusion kit, the blood transfusion system, the blood transfusion kit for emergency blood transfusion, and the method of using the blood transfusion kit are more convenient to use by enabling the transfusion of whole blood easily during the emergency or the like while performing safe blood transfusion during the normal time.

DESCRIPTION OF EMBODIMENTS

Hereinafter, preferred embodiments of the present invention will be described in detail with reference to the accompanying drawings.

First Embodiment

Figure 1:
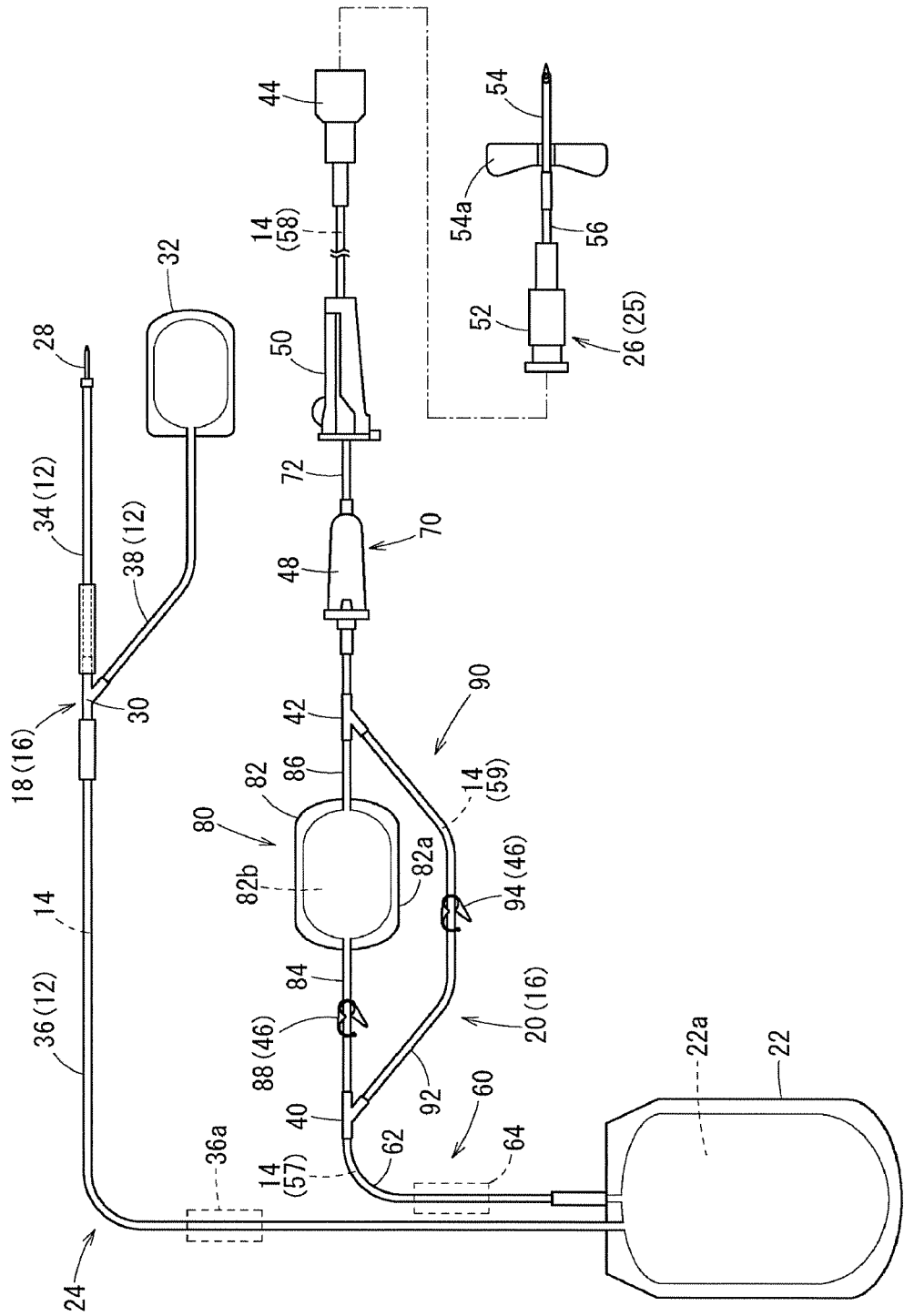
FIG. 1 is an explanatory view illustrating an overall configuration of a blood transfusion system according to a first embodiment of the present invention.

As illustrated in FIG. 1, a blood transfusion system 10 according to a first embodiment of the present invention has flexibility, and forms a flow path 16 to cause blood to flow using a tube 12 (tube structure) having a channel 14 therein. The flow path 16 includes a blood collection path 18 (blood collection channel) to collect blood from a donor and an administration path 20 (administration channel) to administer blood to a patient (blood transfusion target). Each of the blood collection path 18 and the administration path 20 is connected to a blood bag 22 that temporarily stores blood. Note that the tube structure forming the flow path 16 includes various tubular members capable of causing a liquid to flow in addition to the tube 12. For example, three-port connectors 30, 40, and 42, a drip chamber 48, and the like, which will be described later, also correspond to the tube structure.

In addition, the blood transfusion system 10 is configured as a blood transfusion kit for emergency blood transfusion used at an emergency medical site such as a battlefield and an event of a disaster. The blood transfusion system 10 provides a set of a main body 24 (blood transfusion kit) including the blood collection path 18, the administration path 20, and the blood bag 22 and a blood introduction kit 26 (administration kit) that is configured as a separate member from the main body 24 and administers blood to a patient. Note that the blood transfusion system 10 may provide only the main body 24 alone without being limited to the provision in such a set. This is because the introduction unit 25 (blood transfusion unit) administering the liquid to the patient is sometimes constructed in advance before blood transfusion.

Then, the administration path 20 of the blood transfusion system 10 (the main body 24) includes a plurality of paths (a first path 80 and a second path 90) for flow of blood in parallel, so that a blood transfusion route can be easily switched according to a condition of the patient at the time of blood transfusion. That is, the blood transfusion system 10 is configured to trap leukocytes by a leukocyte removal filter 82 using the first path 80 during the normal time to administer the other blood components (erythrocytes, platelets, and plasma) to the patient. On the other hand, the blood transfusion system 10 is configured to administer blood (whole blood) from which leukocytes have not been removed to the patient in an emergency using the second path 90. Hereinafter, the blood transfusion system 10 will be specifically described.

The blood collection path 18 of the blood transfusion system 10 includes the above-described tube 12, a blood collection needle 28 (a blood collection unit), and the three-port connector 30, and can cause blood to flow from a donor (not illustrated) to the blood bag 22 by interconnecting these parts. In addition, the blood collection path 18 is provided with an initial flow blood bag 32 configured to store initial flow blood of the donor.

The tube 12 of the blood collection path 18 includes: a blood collection tube 34 extending between the blood collection needle 28 and the three-port connector 30; a blood-collection-side blood bag connection tube 36 extending between the three-port connector 30 and the blood bag 22; and an initial flow blood bag connection tube 38 extending between the three-port connector 30 and the initial flow blood bag 32. That is, the three-port connector 30 is a joint that connects the blood collection tube 34, the blood-collection-side blood bag connection tube 36, and the initial flow blood bag connection tube 38. In addition, each of the tubes 34, 36, and 38 may be provided with a clamp in advance although not illustrated.

The blood collection needle 28 of the blood collection path 18 is inserted and placed in the donor by the medical staff as blood is collected from the donor. In addition, a blood collection pump 36a that suctions the blood of the donor is disposed at a predetermined point of the blood-collection-side blood bag connection tube 36. At the start of the suction, the blood of the donor is first stored in the initial flow blood bag 32 via the blood collection tube 34, the three-port connector 30, and the initial flow blood bag connection tube 38. Then, when a predetermined amount of initial flow blood is stored in the initial flow blood bag 32, the initial flow blood bag connection tube 38 is closed by a clamp (not illustrated). As a result, the blood of the donor is stored in the blood bag 22 via the blood collection tube 34, the three-port connector 30, and the blood-collection-side blood bag connection tube 36.

The blood bag 22 has an internal space 22a in which a predetermined amount of blood can be stored, and is hung on a stand (not illustrated), for example, with a connecting portion with the tube 12 facing downward. An anticoagulant that suppresses coagulation of blood collected from the donor is injected into the internal space 22a of the blood bag 22 in advance. Examples of the anticoagulant include acid-citrate-dextrose (ACD) and CPD.

Further, the administration path 20 of the blood transfusion system 10 is provided with the leukocyte removal filter 82, the first three-port connector 40, the second three-port connector 42, and an end connector 44, in addition to the above-described tube 12. In addition, a plurality of clamps 46, the drip chamber 48, and a roller clamp 50 are provided at appropriate positions on the administration path 20.

When assembling these respective members (tube structures), the administration path 20 constructs an upstream path 60 and a downstream path 70 on the downstream side (closer to the patient) from the upstream path 60, and constructs the first path 80 and the second path 90 between these paths 60 and 70.

More specifically, the tube 12 of the administration path 20 includes an administration-side blood bag connection tube 62, a filter upstream tube 84, a filter downstream tube 86, an administration downstream tube 72, and a bypass tube 92.

The administration-side blood bag connection tube 62 extends by a predetermined length, has one end connected to the blood bag 22 and the other end connected to the first three-port connector 40, and forms the upstream path 60 that guides blood from the blood bag 22 to the first path 80 or the second path 90. An administration pump 64 causing blood to flow at the time of administration of blood may be set at an intermediate position of the administration-side blood bag connection tube 62. In particular, blood transfusion passing through the second path 90 to be described below administers a large amount of blood, and thus, the administration pump 64 may be set in the bypass tube 92.

The filter upstream tube 84 and the filter downstream tube 86 form the first path 80, and the leukocyte removal filter 82 is provided therebetween. The filter upstream tube 84 has one end connected to the first three-port connector 40 and the other end connected to the leukocyte removal filter 82. That is, the first channel 57 is formed inside the administration-side blood bag connection tube 62, the filter upstream tube 84, and the first three-port connector 40. In this case, the first three-port connector 40 forms a branch point of the first channel 57. Further, the filter downstream tube 86 has one end connected to the leukocyte removal filter 82 and the other end connected to the second three-port connector 42.

A first clamp 88, which is one of the plurality of clamps 46, is provided at an intermediate position of the filter upstream tube 84. The first clamp 88 enables the medical staff to change the opening and closing of the channel 14 (that is, the first path 80) of the filter upstream tube 84.

The leukocyte removal filter 82 has a bag 82a having a cavity communicating with each of the channels 14 of the filter upstream tube 84 and the filter downstream tube 86 and a filter main body 82b provided so as to divide (block) the cavity inside the bag 82a. For example, the filter main body 82b is configured using a mesh-like filter including a plurality of holes having a smaller diameter than leukocytes. A plurality of the mesh-like filters may be stacked. Note that the filter main body 82b may have a function of removing other minute substances contained in blood.

With this filter main body 82b, the leukocyte removal filter 82 removes leukocytes from blood supplied to the cavity (that is, filters the blood), and allows other blood components (plasma, platelets, erythrocytes, and the like) to pass therethrough. That is, the blood transfusion system 10 passes through the leukocyte removal filter 82 during normal blood transfusion, thereby suppressing transfusion side effects (virus infection, fever, and the like) caused by leukocytes.

The administration downstream tube 72 has one end connected to the second three-port connector 42 and the other end (the most downstream side of the downstream path 70) provided with the end connector 44 (a blood transfusion unit: a connecting portion). That is, the second channel 58 is formed inside the filter downstream tube 86, the administration downstream tube 72, and the second three-port connector 42. As the end connector 44, a general-purpose female lock connector conforming to the standard of medical devices for blood transfusion is applied. The main body 24 is configured to be connectable to the blood introduction kit 26 by the end connector 44.

The blood introduction kit 26 is a member that constructs the introduction unit 25 on the patient, and is provided by being packaged integrally with the main body 24. The blood introduction kit 26 includes: an end connector 52 (connected portion); an administration needle (administration portion) 54 which pieces (is inserted into) the patient to be placed; and a connection tube 56 that has one end connected to the end connector 52 and the other end connected to the administration needle 54.

For example, a male lock connector is applied as the end connector 52 of the blood introduction kit 26, and the end connector 52 is connected to the end connector 44 of the main body 24. The administration needle 54 is configured as a winged needle having a pair of wings 54a. In this case, the pair of wings 54a serves as a grasping unit with which the medical staff such as a doctor and a nurse performs a grasping and puncturing operation, and is spread on a body surface of the donor during blood donation to serve as a fixing unit used at the time of fixing with a tape or a bandage. Note that the administration needle 54 is not limited to the winged needle, and various structures can be applied.

In addition, the drip chamber 48 and the roller clamp 50 are provided at an intermediate position of the administration downstream tube 72. The drip chamber 48 enables confirmation of an administration speed of blood to be administered to the patient. The roller clamp 50 opens and closes the channel 14 of the administration downstream tube 72 as the medical staff operates to rotate a roller. For example, after implementation of a priming step, the roller clamp 50 is operated so as to block the channel 14 until the end connector 44 of the main body 24 and the end connector 52 of the blood introduction kit 26 are connected.

Further, the bypass tube 92 of the blood transfusion system 10 is provided so as to form the second path 90 and bypass the leukocyte removal filter 82. Specifically, the bypass tube 92 has one end connected to the first three-port connector 40 and the other end connected to the second three-port connector 42. That is, the bypass channel 59 is formed inside the bypass tube 92, the first three-port connector 40, and the second three-port connector 42. The bypass tube 92 is formed to be longer than the total length of the filter upstream tube 84 and the filter downstream tube 86.

A second clamp 94 is provided at an intermediate position of the bypass tube 92. The second clamp 94 enables a medical staff to change the opening and closing of the channel 14 (that is, the second path 90) of the bypass tube 92.

Note that the first path 80 is used during the normal time so that the second path 90 (that is, the bypass tube 92) is in the state of blocking the channel 14 by the second clamp 94 as will be described later. Thus, it is more preferable to apply a normally closed structure to the second clamp 94, and it is preferable that the bypass tube 92 also have physical properties that can easily be elastically restored from a long-term closed state of the channel 14.

As material forming the above tube 12, a soft resin material is suitable, and examples thereof include a fluorine-based resin such as polytetrafluoroethylene (PTFE), ethylene-tetrafluoroethylene copolymer (ETFE) and perfluoroalkoxy fluorine resin (PFA), an olefin-based resin such as polyethylene and polypropylene or a mixture thereof, polyurethane, polyester, polyamide, polyether nylon resin, a mixture of the olefin-based resin and ethylene-vinyl acetate copolymer, and the like.

Note that the blood transfusion system 10 according to the present embodiment can, of course, apply various members that can be assembled to the flow path 16 in addition to the members described above.

The blood transfusion system 10 according to the first embodiment is basically configured as described above, and a method of using the same will be described hereinafter.

The blood transfusion system 10 is used, for example, at an emergency medical site such as a battlefield and an event of a disaster in order to collect blood from a donor and immediately transfuse the blood to a patient. Note that a step of connecting the blood collection path 18 to the donor and storing (collecting) the blood in the blood bag 22 can be performed by a known method, and the description thereof will be omitted.

Figure 2:
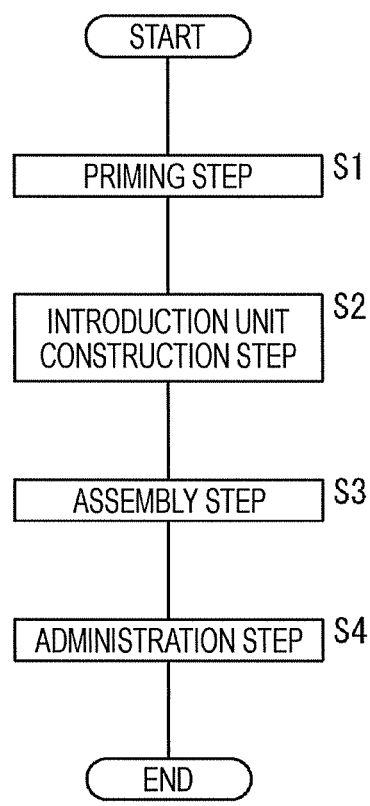
FIG. 2 is a flowchart illustrating a method of using the blood transfusion system in FIG. 1.

For example, during blood transfusion to a patient, a priming step of the main body 24, an introduction unit construction step of constructing the introduction unit 25 on the patient using the blood introduction kit 26, an assembly step of connecting the main body 24 and the blood introduction kit 26, and an administration step of administering blood are performed as illustrated in FIG. 2.

In the priming step (Step S1), blood is allowed to flow out of the blood bag 22 and is caused to flow through the respective channels 14 of the administration-side blood bag connection tube 62, the filter upstream tube 84, the filter downstream tube 86, the administration downstream tube 72, and the bypass tube 92. At this time, the roller clamp 50 opens the administration downstream tube 72, and the blood reaches the vicinity of the other end (end connector 44) of the administration downstream tube 72 while pushing out the air existing inside the respective channels 14. Then, when the blood fills the channels 14, the roller clamp 50 is closed to temporarily block the channels 14.

In the introduction unit construction step (Step S2), the medical staff inserts and places the administration needle 54 of the blood introduction kit 26 into the patient, and secures the channel 14 to a blood vessel of the patient via the blood introduction kit 26. When inserting the administration needle 54, the blood of the patient flashes back, so that the blood reaches the end connector 52 from the connection tube 56, and the air of the blood introduction kit 26 escapes.

Thus, in the assembly step (Step S3), the end connector 44 of the main body 24 and the end connector 52 of the blood introduction kit 26 are connected so that the administration path 20 of the main body 24 communicates with the blood vessel of the patient while excluding air. Therefore, blood containing substantially no air is administered to the patient in the administration step after the assembly step.

Figure 3A:
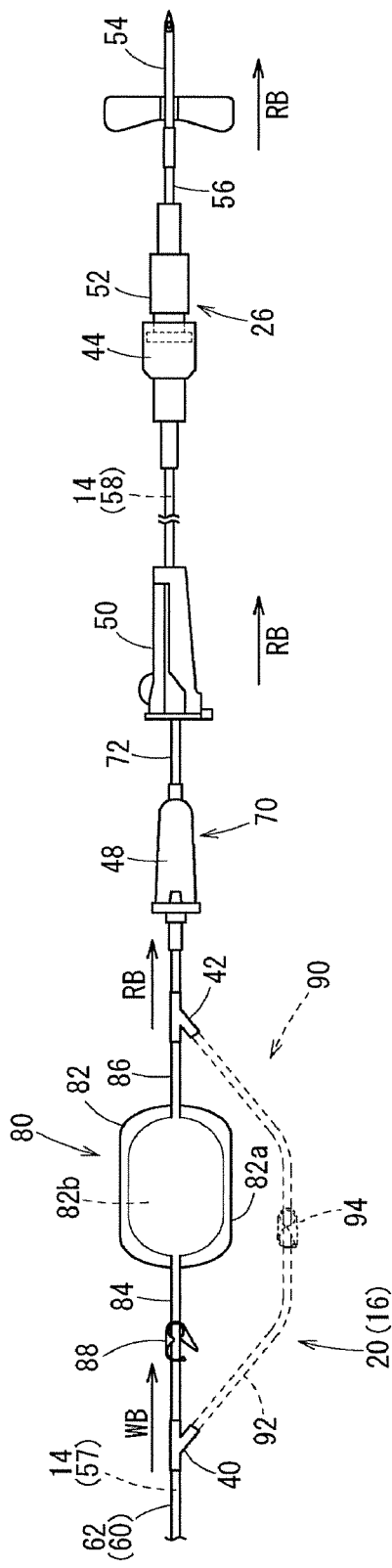
FIG. 3A is an explanatory view illustrating a flow state of blood using a first path.

In the administration step (Step S4), blood is transfused into the patient using the first path 80 basically (normally). That is, as illustrated in FIG. 3A, the medical staff closes the second path 90 by closing the second clamp 94 and causes the blood to flow through the first path 80. That is, whole blood WB of the donor flowing out of the blood bag 22 flows from the upstream path 60 to the first path 80, and passes through the leukocyte removal filter 82, and then, becomes blood components containing plasma, platelets, and erythrocytes from which leukocytes have been removed (hereinafter, referred to as removed blood RB). Then, the removed blood RB is administered to the patient from the first path 80 via the downstream path 70 and the blood introduction kit 26.

That is, the blood transfusion system 10 selects the first path 80 to cause the blood to pass through the leukocyte removal filter 82 so that the blood transfusion speed is lowered. However, it is possible to perform the safe blood transfusion that continuously administers the removed blood RB to the patient.

Figure 3B:
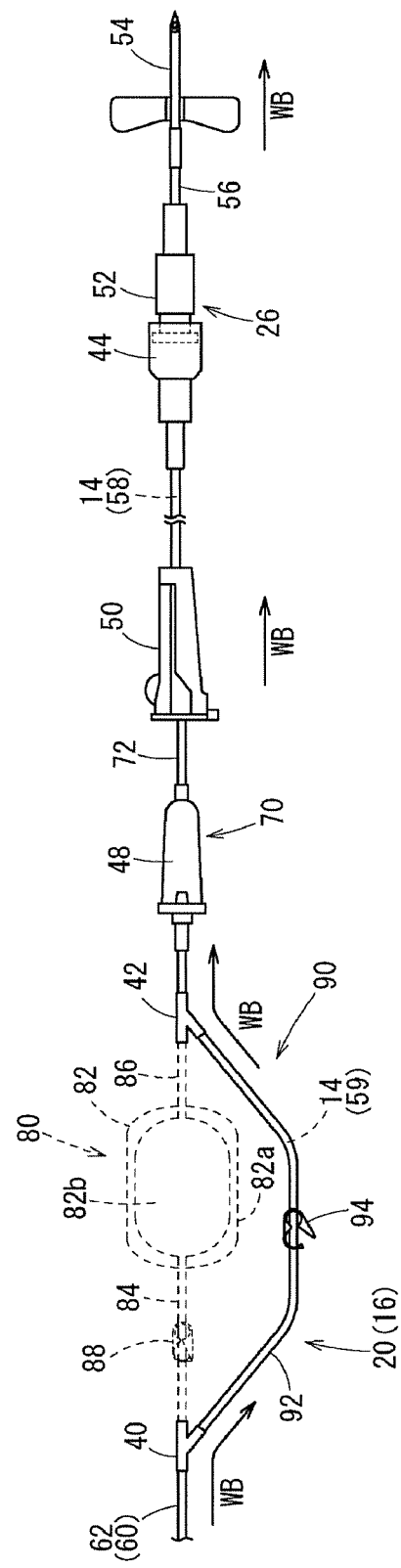
FIG. 3B is an explanatory view illustrating a flow state of blood using a second path.

Further, the blood transfusion system 10 performs blood transfusion to the patient using the second path 90 in a situation where a large amount of blood transfusion is performed rapidly due to a large amount of bleeding of the patient or the like. In this case, the medical staff opens the second path 90 by opening the closed second clamp 94, and closes the first path 80 by closing the first clamp 88. As a result, the flow path 16 (the administration path 20) is switched from the first path 80 to the second path 90 as illustrated in FIG. 3B.

That is, the whole blood WB flows from the blood bag 22 through the upstream path 60, the second path 90, and the downstream path 70 in order, and is administered to the patient. Since the whole blood WB to be administered has not passed through the leukocyte removal filter 82, the leukocytes have not been removed, but a large amount of the whole blood WB is administered to the patient rapidly. As a result, the medical staff can quickly perform life-saving treatment for the suddenly changed patient.

Note that the method of using the blood transfusion system 10 is not limited to the above procedure. For example, if the introduction unit 25 leading to the blood vessel of the patient has been constructed in advance, the end connector 44 of the main body 24 can be connected to the introduction unit 25 (that is, the introduction unit construction step can be omitted).

The blood transfusion system 10 (the blood transfusion kit, the blood transfusion kit for emergency blood transfusion, or method of using the blood transfusion kit) according to the first embodiment described above has the following effects.

The blood transfusion system 10 can transfuse blood from which leukocytes have been removed by the leukocyte removal filter 82 by causing the blood to flow via the first channel 57 and the second channel 58 during the normal time. As a result, it is possible to perform the safe blood transfusion that suppresses the transfusion side effects of the patient. In addition, the blood transfusion system 10 can rapidly administer a large amount of blood without passing through the leukocyte removal filter 82 by causing the blood to flow through the bypass channel 59 during the emergency. That is, the blood transfusion system 10 can easily switch between the first path 80 and the second path 90, and thus, becomes more convenient to use so that it is possible to reduce the burden on the medical staff and to speed up the medical treatment.

In addition, the blood transfusion system 10 can rapidly perform a large amount of blood transfusion to the patient since the upstream path 60, the downstream path 70, and the second path 90 are configured to have no blood stagnation (for example, there is no configuration such as storing blood components in a bag). Further, the blood transfusion system 10 can easily switch between the closing and opening of the channel 14 as the medical staff operates the first clamp 88 provided in the first path 80 and the second clamp 94 provided in the second path 90.

Then, the end connector 44 of the main body 24 can be easily connected to the introduction unit 25 constructed for the patient, so that the blood transfusion can be started for a shorter period of time. In addition, since the upstream path 60 is directly connected to the blood bag 22, the blood transfusion system 10 can immediately administer the blood stored in the blood bag 22 to the patient, and can perform the blood transfusion more quickly. Furthermore, the blood transfusion system 10 can immediately transfuse the blood from the blood bag 22 after storing the blood of the donor since the blood collection path 18 is directly connected to the blood bag 22.

Second Embodiment

Figure 4:
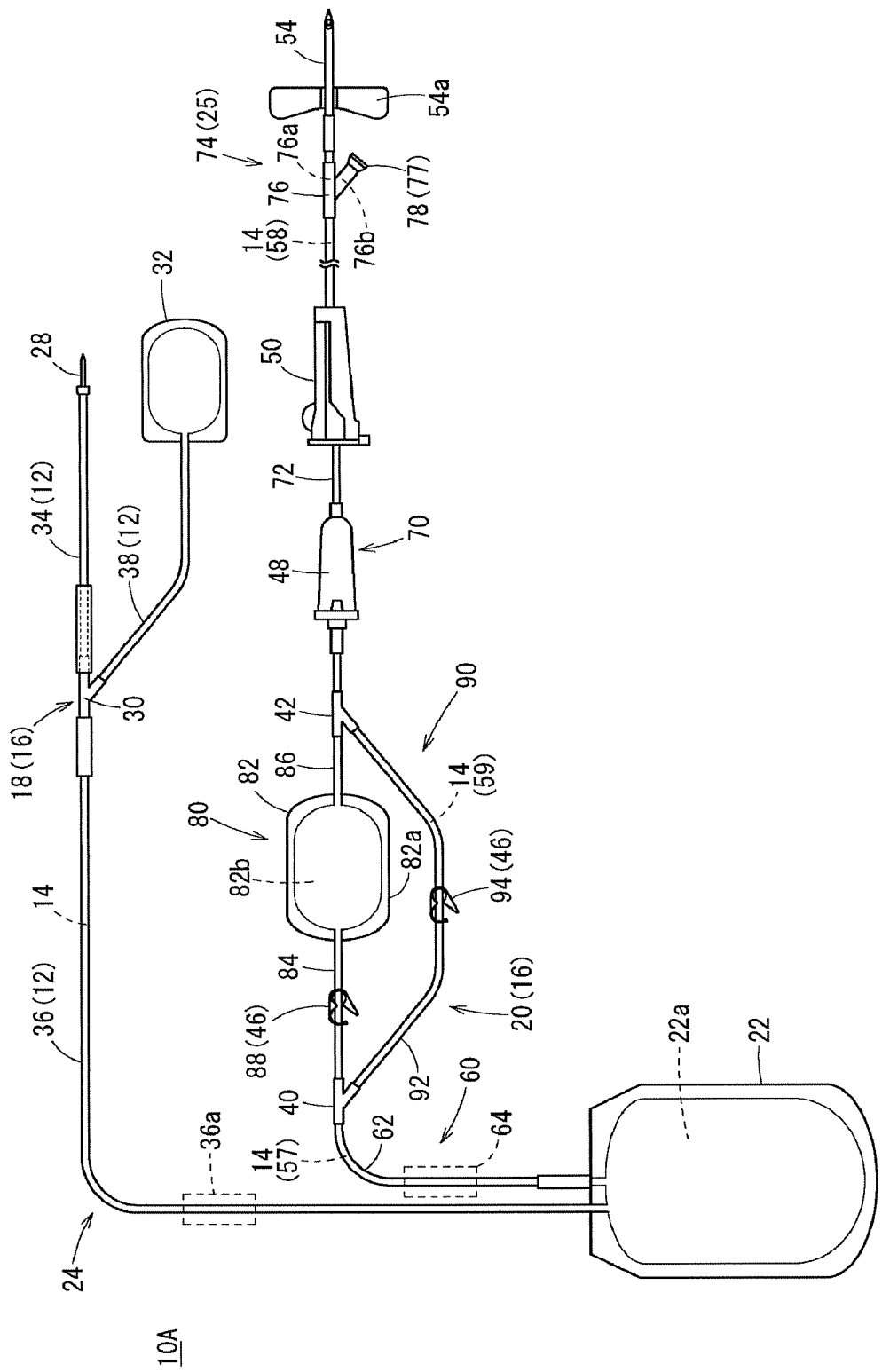
FIG. 4 is an explanatory view illustrating an overall configuration of a blood transfusion system according to a second embodiment of the present invention.

A blood transfusion system 10A according to a second embodiment of the present invention is different from the blood transfusion system 10 according to the first embodiment in terms that an introduction structure 74 that constructs the introduction unit 25 is provided integrally on the downstream side of the administration path 20 (the downstream path 70) as illustrated in FIG. 4. Note that, in the following description, the same configurations or elements having the same functions as those in the above embodiment will be denoted by the same reference signs, and detailed descriptions thereof will be omitted.

Specifically, the introduction structure 74 of the downstream path 70 is located on the downstream side of the roller clamp 50 of the administration downstream tube 72, and includes a male closed connector 76 and the administration needle 54 (the blood transfusion unit: the winged needle). Note that the blood collection path 18, the upstream path 60, the first path 80, and the second path 90 of the blood transfusion system 10A have the same configurations as those in the first embodiment.

The male closed connector 76 includes a main channel 76a that connects the administration downstream tube 72 and the administration needle 54 and is configured as a three-port type including a sub-channel 76b branching from the main channel 76a. Further, the male closed connector 76 includes a cap 78 with an air vent filter, which is an air vent unit 77, so as to close the sub-channel 76b.

The cap 78 with the air vent filter discharges air guided to the sub-channel 76b by a filter (not illustrated) facing the sub-channel 76b in the male closed connector 76 and regulates discharge of blood. In addition, when the cap 78 with the air vent filter is removed, the male closed connector 76 self-blocks the sub-channel 76b of the male closed connector 76. As a result, there is no outflow of blood from the male closed connector 76, and the blood favorably flows to the administration needle 54.

The administration needle 54 is provided at a position near the downstream side of the male closed connector 76, and supplies blood that is substantially free of air to the patient after priming from the blood bag 22.

The blood transfusion system 10A according to the second embodiment is basically configured as described above. When this blood transfusion system 10A is used, a priming step, an introduction unit construction step, and an administration step are performed (a flow excluding Step S3 in FIG. 2).

In the priming step, blood is caused to flow out of the blood bag 22 to the administration path 20, and the blood flows while pushing out the air existing in the respective channels 14. The air in the respective channels 14 flows out to the outside through the cap 78 with the air vent filter, and as a result, the blood substantially fills the channels 14 of the administration path 20. That is, the blood in the blood bag 22 can be automatically prime the channel 14 up to the male closed connector 76 in the administration path 20 by the air vent unit 77.

In addition, in the introduction unit construction step, the medical staff inserts and places the administration needle 54 of the blood transfusion system 10A into a blood vessel of the patient. As a result, the blood of the patient is flushed back from the administration needle 54, and air on the distal end side of the male closed connector 76 flows out to the outside through the cap 78 with the air vent filter. Then, the blood primed up to the downstream path 70 and the blood that has been flushed back are mixed. After the priming step and the introduction unit construction step, the cap 78 with the air vent filter is removed to block the sub-channel 76b of the male closed connector 76.

As a result, the blood containing almost no air can be administered to the patient in the administration step. In addition, blood transfusion via the first path 80 during the normal time and blood transfusion via the second path 90 during the emergency can be selectively performed in the administration step, which is similar to the first embodiment.

As described above, the same effects as those in the first embodiment can be obtained in the blood transfusion system 10A according to the second embodiment. In particular, since the blood transfusion system 10A is configured such that the administration needle 54 is directly connected to the downstream path 70, the step of connecting the end connectors 44 and 52 in the first embodiment can be omitted. As a result, it is possible to start the administration of blood more quickly. In addition, the blood transfusion system 10A uses the air vent unit 77 to simplify (automate) the operation of the priming step, and thus, the convenience is further improved.

Incidentally, the present invention is not limited to the above-described embodiments, and various modifications are possible in accordance with a gist of the invention. For example, the switching between the first path 80 and the second path 90 is not limited to the opening and closing operation of the channel 14 using the first clamp 88 and the second clamp 94. As an example, a three-way cock that can switch a communication state between the upstream path 60 and the first path 80 and a communication state between the upstream path 60 and the second path 90 may be applied, instead of the first three-port connector 40.

In addition, the first path 80 may be set in a centrifugal separator or the like so that centrifugal separation of whole blood is performed, and separated blood components (such as plasma and platelets) are caused to flow to the downstream path 70.

Furthermore, the administration path 20 is not limited to the configuration of being directly connected to the blood bag 22, but may be configured to be connect to the separately supplied blood bag 22 by a connection mechanism (not illustrated) such as a bottle needle. That is, the blood transfusion systems 10 and 10A according to the present invention can be configured only using the administration path 20.

Figure 5:
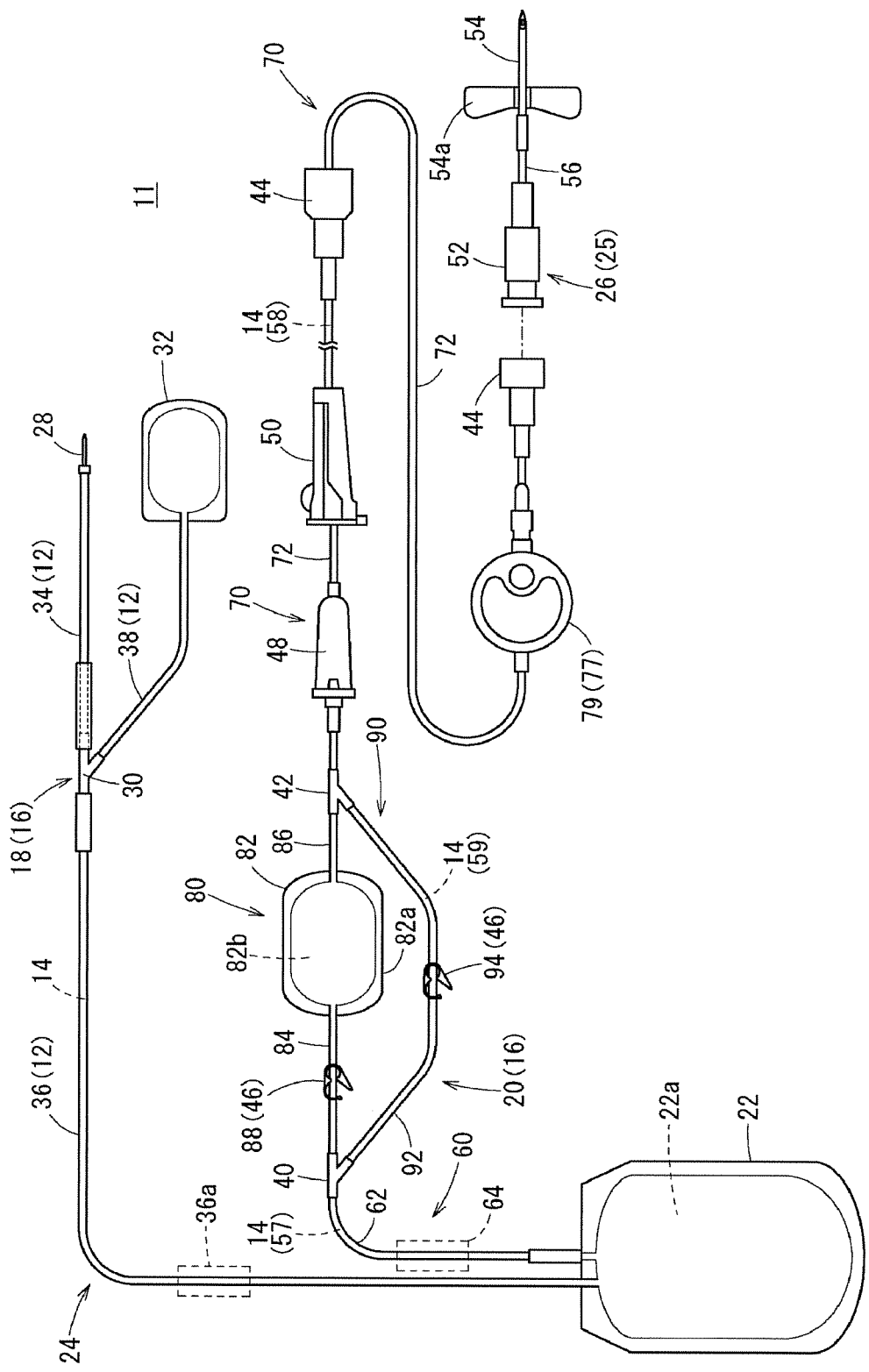
FIG. 5 is an explanatory view illustrating an overall configuration of a blood transfusion system according to a modification.

A blood transfusion system 11 according to a modification illustrated in FIG. 5 is different from the blood transfusion system 10 according to the first embodiment in terms of including the air vent filter 79 (air vent unit 77) at a position near the upstream side of the end connector 44. Note that the configurations other than the air vent unit 77 are the same as those of the blood transfusion system 10.

The air vent filter 79 discharges air in the downstream path 70 and regulates discharge of blood. As a result, the priming can be automatically performed even in the blood transfusion system 11 having the end connector 44.

The invention claimed is:

1. A blood transfusion kit comprising: a first blood bag for containing blood from a donor, the first blood bag including a first port and a second port; a filter that removes configured to remove leukocytes in blood from the first blood bag; a blood transfusion unit configured to transfuse blood from which the leukocytes have been removed by the filter to a blood transfusion target; a first channel connecting the second port of the first blood bag and the filter; a second channel connecting the filter and the blood transfusion unit; a bypass channel connected between a first branch point of the first channel and a second branch point of the second channel and that enables blood in the first blood bag to bypass the filter; a blood collection tube connected between a third branch point and the first port of the first blood bag; a second blood bag configured to store blood from the donor; a blood collection needle for insertion into the donor; a first tube that connects the third branch point and the second blood bag; a second tube that connects the third branch point and the blood collection needle; and a first pump fluidly coupled to the blood collection tube and configured to pump blood from the donor into the first blood bag through the first port, wherein the first pump is also configured to pump blood from the donor into the second blood bag.

2. The blood transfusion kit according to claim 1, wherein a downstream side of the first channel from the first branch point and the bypass channel are provided respectively with clamps capable of opening and closing the first channel and the bypass channel.

3. The blood transfusion kit according to claim 1, wherein the blood transfusion unit is provided at an end of the second channel, and includes an end connector attachable to an introduction unit constructed for the blood transfusion target.

4. The blood transfusion kit according to claim 3, wherein the second channel is provided with an air vent unit that discharges air inside the second channel and regulates outflow of blood inside the second channel.

5. The blood transfusion kit according to claim 1, wherein the blood transfusion unit comprises an administration needle that is provided at an end of the second channel.

6. The blood transfusion kit according to claim 1, wherein the first channel and the bypass channel are coupled by a three-way cock at the first branch point that switches a communication state between the filter and the bypass channel.

7. The blood transfusion kit according to claim 1, wherein the second blood bag has a single port connected to the first tube.

8. The blood transfusion kit according to claim 1, wherein the first port and the second port of the first blood bag are on a same side of the first blood bag.

9. The blood transfusion kit according to claim 8, wherein the first port is an inlet through which blood from the donor flows into the first blood bag.

10. The blood transfusion kit according to claim 9, wherein the second port is an outlet through which blood in the first blood bag flows into the first channel.

11. The blood transfusion kit according to claim 10, further comprising:
a second pump fluidly coupled to the first channel and that pumps blood from the first blood bag through the second port into the first channel.

12. The blood transfusion kit according to claim 8, further comprising:
a clamp that opens and closes the blood collection tube.

13. The blood transfusion kit according to claim 8, wherein the third branch point comprises a three-port connector.

14. The blood transfusion kit according to claim 1, further comprising:

a second pump fluidly coupled to the first channel and that pumps blood from the first blood bag through the second port into the first channel.

15. A blood transfusion system comprising: a blood collection needle for insertion into a donor of blood; a first blood bag for containing blood collected from the donor, the first blood bag including a first port and a second port; a second blood bag; a filter configured to remove leukocytes in blood from the first blood bag; a blood transfusion unit; a first channel connecting the second port of the first blood bag and the filter; a second channel connecting the filter and the blood transfusion unit; and a bypass channel connected between a first branch point of the first channel and a second branch point of the second channel and that enables blood in the first blood bag to bypass the filter; a first connecting portion coupled to the second channel; a second connecting portion coupled to the blood transfusion unit, the second connecting portion being removably connected to the first connecting portion; a blood collection tube connected between a third branch point and the first port of the first blood bag; a first tube that connects the third branch point and the second blood bag; a second tube that connects the third branch point and the blood collection needle; and a first pump fluidly coupled to the blood collection tube and configured to pump blood from the donor into the first blood bag through the first port, wherein the first pump is also configured to pump blood from the donor into the second blood bag.

16. The blood transfusion system according to claim 15, wherein
the first channel has a clamp capable of opening and closing the first channel between the first branch point and the filter.

17. The blood transfusion system according to claim 15, wherein
the bypass channel has a clamp capable of opening and closing the bypass channel.

18. A blood transfusion kit for emergency blood transfusion comprising: a main body that collects blood; and an administration kit that administers blood collected by the main body to a blood transfusion target in order to transfuse blood, wherein the main body and the administration kit form a channel through which blood flows, and wherein the main body includes: a blood collection needle for insertion into a donor; a first blood bag for containing blood collected from the donor, the first blood bag including a first port and a second port; a second blood bag that stores configured to store blood from the donor; a filter that removes configured to remove leukocytes in blood from the first blood bag; a first channel connecting the second port of the first blood bag and the filter; a second channel that extends on a downstream side of the filter and is provided with a connecting portion, connected to the administration kit, at an end; a bypass channel connected between a first branch point of the first channel and a second branch point of the second channel and that enables blood in the first blood bag to bypass the filter; a blood collection tube connected between a third branch point and the first port of the first blood bag; a first tube that connects the third branch point and the second blood bag; and a second tube that connects the third branch point and the blood collection needle; and a first pump fluidly coupled to the blood collection tube and configured to pump blood from the donor into the first blood bag through the first port, wherein the first pump is also configured to pump blood from the donor into the second blood bag, wherein the administration kit includes: an administration portion configured to transfuse blood into the blood transfusion target; and a connected portion configured to connect to the connecting portion of the main body, wherein the main body and the administration kit are integrally packaged.

19. The blood transfusion kit according to claim 18, further comprising:
a second pump fluidly coupled to the first channel and that pumps blood from the first blood bag through the second port into the first channel.

20. A method of using a blood transfusion kit, through which blood flows using a tube structure and administers blood to a blood transfusion target, the blood transfusion kit including:
a first blood bag for containing blood from a donor, the first blood bag including a first port and a second port;
a filter that removes leukocytes in blood from the first blood bag;
a blood transfusion unit configured to transfuse blood from which the leukocytes have been removed by the filter to the blood transfusion target;
a first channel connecting the first blood bag and the filter;
a second channel connecting the filter and the blood transfusion unit;
a bypass channel connected between a first branch point of the first channel and a second branch point of the second channel and that enables blood in the first blood bag to bypass the filter;
a blood collection tube connected between a third branch point and the first port of the first blood bag;
a second blood bag that stores blood from the donor;
a blood collection needle for insertion into the donor;
a first tube that connects the third branch point and the second blood bag; and
a second tube that connects the third branch point and the blood collection needle, the method comprising:
operating a pump to pump blood into the second blood bag through the second tube, the third branch point, and the first tube until a predetermined amount of blood is stored in the second blood bag;
clamping the first tube when the predetermined amount of blood stored in the second blood bag is reached;
operating, while the first tube is clamped, the pump to pump blood into the first blood bag through the first port; and
selectively switching between a first state in which blood is administered through the filter by opening the first channel and closing the bypass channel, and a second state in which blood is administered without passing through the filter by opening the bypass channel and closing the first channel downstream from the first branch point, when using the blood transfusion kit.

* * * * *